US009949721B2

(12) United States Patent
Tu et al.

(10) Patent No.: US 9,949,721 B2
(45) Date of Patent: Apr. 24, 2018

(54) ACOUSTIC DIODES AND METHODS OF USING SAME

(71) Applicant: NANJING UNIVERSITY, Nanjing, Jiangsu (CN)

(72) Inventors: Juan Tu, Jiangsu (CN); Bin Liang, Jiangsu (CN); Jianchun Cheng, Jiangsu (CN); Dong Zhang, Jiangsu (CN); Yong Li, Jiangsu (CN); Xiasheng Guo, Jiangsu (CN)

(73) Assignee: Nanjing University, Nanjing Jiangsu (CN)

( * ) Notice: Subject to any disclaimer, the term of this patent is extended or adjusted under 35 U.S.C. 154(b) by 368 days.

(21) Appl. No.: 14/779,172

(22) PCT Filed: Mar. 22, 2013

(86) PCT No.: PCT/CN2013/073064
§ 371 (c)(1),
(2) Date: Sep. 22, 2015

(87) PCT Pub. No.: WO2014/146294
PCT Pub. Date: Sep. 25, 2014

(65) Prior Publication Data
US 2016/0051227 A1    Feb. 25, 2016

(51) Int. Cl.
*G10K 11/18* (2006.01)
*A61B 8/00* (2006.01)
(Continued)

(52) U.S. Cl.
CPC .............. *A61B 8/4494* (2013.01); *A61B 8/14* (2013.01); *A61B 8/4483* (2013.01);
(Continued)

(58) Field of Classification Search
CPC ..................................................... G10K 11/18
See application file for complete search history.

(56) References Cited

U.S. PATENT DOCUMENTS 4,048,594 A    9/1977  Weglein
4,618,796 A    10/1986 Riedlinger
(Continued)

FOREIGN PATENT DOCUMENTS

CN         102175300 A        9/2011

OTHER PUBLICATIONS

Li. Y., et al., "Unidirectional acoustic transmission based on source pattern reconstruction," Journal of Applied Physics, vol. 112, No. 6, pp. 8 (2012).
(Continued)

*Primary Examiner* — Hovhannes Baghdasaryan
(74) *Attorney, Agent, or Firm* — Pepper Hamilton LLP

(57) ABSTRACT

Acoustic diodes, devices incorporating such diodes and methods of using such devices are disclosed. An acoustic diode may include a periodic acoustic grating and a uniform plate. The periodic acoustic grating may include a plurality of gratings. The uniform plate may foe separated from the periodic acoustic grating by a resonant cavity. The acoustic diode may be configured to have a first transmission efficiency for acoustic waves incident on the periodic acoustic grating that is greater than a second transmission efficiency for acoustic waves incident on the uniform plate. The acoustic waves may have a wavelength within a range of wavelengths. Devices incorporating the acoustic diode may include medical imaging devices, such as ultrasound devices, and noise reduction devices.

29 Claims, 5 Drawing Sheets

(51) Int. Cl.
*H03H 9/02* (2006.01)
*G01N 29/06* (2006.01)
*A61B 8/14* (2006.01)
*A61B 8/08* (2006.01)

(52) U.S. Cl.
CPC ....... *A61B 8/5269* (2013.01); *G01N 29/0654* (2013.01); *G10K 11/18* (2013.01); *H03H 9/02* (2013.01)

(56) References Cited

U.S. PATENT DOCUMENTS

| | | | |
|---|---|---|---|
| 4,884,998 A | 12/1989 | Miranti, Jr. | |
| 8,511,423 B2 | 8/2013 | Cheng et al. | |
| 2011/0282204 A1 | 11/2011 | Shibata et al. | |
| 2012/0146745 A1 | 6/2012 | Wong et al. | |
| 2012/0186904 A1* | 7/2012 | Cheng | G10K 11/04 181/175 |
| 2013/0025961 A1* | 1/2013 | Koh | F16F 15/02 181/207 |
| 2013/0112496 A1* | 5/2013 | Neogi | G10K 11/04 181/175 |

OTHER PUBLICATIONS

Liang. B., and Cheng J-C., "One-way street for acoustic waves: Theoretical design and experimental realization of acoustic diodes," Physics, vol. 41, Issue. 8, pp. 536-541 (Aug. 12, 2012) (English Abstract).

Bhattacharya et al., Coincidence effect with sound waves in a finite plate, *Journal of Sound and Vibration* (Sep. 22, 1971), 18(2):157-169.

He et al., Asymmetric acoustic gratings, *Applied Physics Letters* (Feb. 23, 2011), 98(8):083505:1-083505:3.

International Search Report and Written Opinion for International Patent Application No. PCT/CN2013/073064 dated Jan. 2, 2014.

Li et al., Tunable Unidirectional Sound Propagation through a Sonic-Crystal-Based Acoustic Diode, *Physical Review Letters* (Feb. 23, 2011), 106(8):084301:1-084301:4.

* cited by examiner

ACOUSTIC DIODES AND METHODS OF USING SAME

CROSS-REFERENCE TO RELATED APPLICATION

This application is a U.S. national stage filing under 35 U.S.C. § 371 of International Application No. PCT/CN2013/073064, filed on Mar. 22, 2013 and entitled "Acoustic Diodes and Methods of Using Same," the content of which is incorporated herein by reference in its entirety.

BACKGROUND

Electrical diodes, components that allow current to flow in only one direction, are commonplace in electrical and computer systems. However, an analogue in the acoustic realm was lacking until very recently. An acoustic diode enables sound waves to travel through the diode in a first direction, but impedes sound waves front travelling in an opposite direction.

Although considerable efforts have been dedicated to demonstrating acoustic diode concepts, both theoretically and experimentally, obstacles have limited practical breakthroughs in the field. In particular, acoustic diodes that are simple to fabricate and capable of being made in small sizes have been lacking to date.

SUMMARY

This disclosure is not limited to the particular systems, devices and methods described, as these may vary. The terminology used in the description is for the purpose of describing the particular versions or embodiments only, and is not intended to limit the scope.

As used in this document, the singular forms "a," "an/" and "the" include plural references unless the context clearly dictates otherwise. Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

In an embodiment, an acoustic diode may include a periodic acoustic grating having a plurality of gratings and a uniform plate separated from the periodic acoustic grating by a resonant cavity. The acoustic diode may be configured to have a first transmission efficiency for acoustic waves incident on the periodic acoustic grating that is greater than a second transmission, efficiency for acoustic waves incident on the uniform plate. The acoustic waves may have a wavelength within a range of wavelengths.

In an embodiment, a medical imaging device may include an acoustic wave generator configured to produce acoustic waves and an acoustic diode. The acoustic diode may include a periodic acoustic grating having a plurality of gratings and a uniform plate separated from the periodic acoustic grating by a resonant cavity. The acoustic diode may be configured to have a first transmission efficiency for acoustic waves incident on the periodic acoustic grating that is greater than a second transmission efficiency for acoustic waves incident on the uniform plate. The acoustic waves may have a wavelength within a range of wavelengths.

In an embodiment, a noise reduction device may include an acoustic diode. The acoustic diode may include a periodic acoustic grating having a plurality of gratings and a uniform plate separated from the periodic acoustic grating by a resonant cavity. The acoustic diode is configured to have a first transmission efficiency for acoustic waves incident on the periodic acoustic grating that is greater than a second transmission efficiency for acoustic waves incident on the uniform plate. The acoustic waves may have a wavelength within a range of wavelengths.

In an embodiment, a method of performing medical imaging may include producing, by an acoustic wave generator in an ultrasound device, an acoustic wave having a wavelength; transmitting the acoustic wave through an acoustic diode, where the acoustic wave passes through a periodic acoustic grating of the acoustic diode and a uniform plate of the acoustic diode, the periodic acoustic grating includes a plurality of gratings, the uniform plate is separated from the periodic acoustic grating by a resonant cavity, and the acoustic diode is configured to have a first transmission efficiency for acoustic waves incident on the periodic acoustic grating that is greater than a second transmission efficiency for acoustic waves incident on the uniform plate; receiving the transmitted acoustic wave at a sensor; and using the received acoustic wave to produce an image.

In an embodiment, a method of reducing noise may include producing an acoustic diode having a periodic acoustic grating and a uniform plate, where the periodic acoustic grating includes a plurality of gratings and the uniform plate is separated from the periodic acoustic grating by a resonant cavity; transmitting at least a portion of a first plurality of acoustic waves incident with the periodic acoustic grating; and reflecting substantially all of a second plurality of acoustic waves incident with the uniform plate of the acoustic diode, whereby a noise level is reduced on a side of the acoustic diode faced by the periodic acoustic grating.

DETAILED DESCRIPTION

In the present disclosure, an acoustic diode is disclosed that includes a double-layered structure having a periodic acoustic grating and a uniform plate separated by a resonant cavity. The operation of the acoustic diode is based on a coincidence effect in acoustics that is intrinsically different from previously identified acoustic diodes. The acoustic diodes described herein may be integrated into other systems, such as ultrasound applications in many fields, such as clinical diagnosis and therapy, noise reduction and the like.

The following terms shall have for the purposes of this application, the respective meanings set forth below.

An "acoustic diode" refers to a device that enables sound waves to travel in a first direction through the device while impeding sound waves from travelling in a second direction through the device that is opposite to the first direction. In other words, an acoustic diode has a transmission efficiency that is substantially higher in the first direction than in the second direction.

Figure 1:
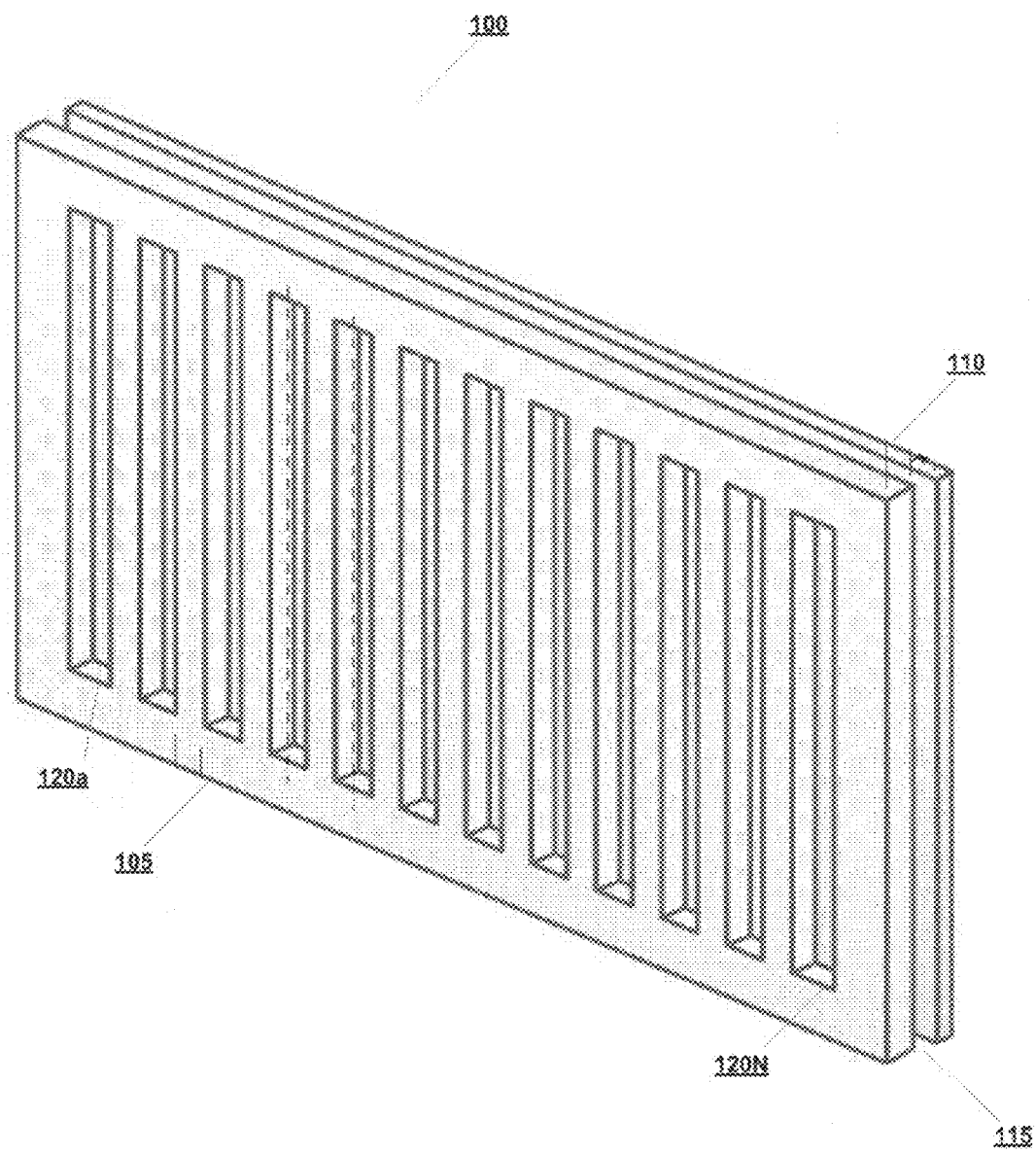
FIG. 1 depicts a schematic of an illustrative acoustic diode according to an embodiment.

FIG. 1 depicts a schematic of an illustrative acoustic diode according to an embodiment. As shown in FIG. 1, the acoustic diode 100 may include a periodic acoustic grating 105 and a uniform plate 110. The periodic acoustic grating 105 may be separated from the uniform plate 110 by a resonant cavity 115. The acoustic diode 100 may be configured to have a first transmission efficiency for acoustic waves incident on the periodic acoustic grating 105 that is greater than a second transmission efficiency for acoustic waves incident on the uniform plate 118. In an embodiment, the acoustic waves may have a wavelength within a range of wavelengths. In an embodiment, the acoustic waves may have a frequency of about 499 kHz to about 678 kHz. In an embodiment, the frequencies of the acoustic waves may be modulated based on the period of the periodic acoustic grating 105 and/or other characteristics of the acoustic diode 100.

Each of the first transmission efficiency and the second transmission efficiency may vary with respect to the frequency of an acoustic wave. However, the first transmission efficiency may be larger or significantly larger than the second transmission efficiency at any wavelength within the range of wavelengths. Specific examples for the first transmission efficiency may include about 2%, about 5%, about 10%, about 15%, about 20%, about 25%, about 30%, about 35%, about 40%, about 45%, about 50%, about 55%, about 60%, about 60.8% and ranges between any two of these values depending upon the wavelength of an acoustic wave. In an embodiment, the first transmission efficiency may be greater than about 10% for at least a portion of the wavelengths associated with the acoustic waves. On average, the first transmission efficiency may be greater than about 20% for at least a portion of the acoustic waves, such as acoustic waves having a frequency of about 499 kHz to about 678 kHz.

Conversely, specific examples for the second transmission efficiency may include about 0%, about 0.25%, about 0.5%, about 0.75%, about 1%, about 1.25%, about 1.5%, about 1.75%, about 2% and ranges between any two of these values depending upon the wavelength of an acoustic wave. In an embodiment, the second transmission efficiency may be less than about 1% for at least a portion of the wavelengths associated with the acoustic waves, such as acoustic waves having a frequency of about 499 kHz to about 678 kHz.

The difference between the first transmission efficiency and the second transmission efficiency represents the effectiveness of the acoustic diode in allowing acoustic waves to pass in a first direction and to impede acoustic waves from passing in an opposing direction. The first transmission efficiency describes the ability for acoustic waves incident on the periodic acoustic grating 105 to pass through the acoustic diode 100. The second transmission efficiency describes the ability for acoustic waves incident on the uniform plate 110 to pass through the acoustic diode 100. Because the first transmission efficiency is larger or substantially larger than the second transmission efficiency, a larger or substantially larger amount of acoustic energy incident on the periodic acoustic grating 105 is passed through the acoustic diode 100 than acoustic energy incident on the uniform plate 110.

The periodic acoustic grating 105 may have a plurality of gratings, such as gratings 120a-N. In an embodiment, at least one grating of the plurality of gratings 120a-N may have a width of about 1.5 millimeters. In an embodiment, a distance between adjacent gratings of the plurality of gratings 120a-N may be about 6 millimeters. The periodic acoustic grating 105 may have a thickness that is substantially equal to a wavelength within the range of wavelengths for the acoustic waves. For example, the periodic acoustic grating 105 may have a thickness of about 3 millimeters. The periodic acoustic grating 105 may be made of a metal or a metal alloy. In an embodiment, the periodic acoustic grating 105 may be made of brass. Additional and/or alternate materials may be used for the periodic acoustic grating 105 within the scope of this disclosure. Alternate materials may affect one or more characteristics of the acoustic diode 100, such as the frequency range at which the acoustic diode has a high transmission efficiency and/or the transmission efficiency in the peak frequency ranges.

The uniform plate 110 may have a thickness that is substantially equal to one-half of a wavelength within the range of wavelengths for the acoustic waves. For example, the uniform plate 110 may have a thickness of about 1.5 millimeters. The uniform plate 110 may be made of a metal or a metal alloy. In an embodiment, the uniform plate 110 may be made of brass. Additional and/or alternate materials may be used for the uniform plate 110 within the scope of this disclosure. Alternate materials may affect one or more characteristics of the acoustic diode 100, such as the frequency range at which the acoustic diode has a high transmission efficiency and/or the transmission efficiency in the peak frequency ranges.

The resonant cavity 115 may be an open cavity between the periodic acoustic grating 105 and the uniform plate 110. In an embodiment, the resonant cavity 115 may have a thickness that is substantially equal to one-half of a wavelength within the range of wavelengths for the acoustic waves. For example, the resonant cavity 115 may have a thickness of about 1.5 millimeters. In other words, the periodic acoustic grating 105 may be separated from the uniform plate 110 by about 1.5 millimeters.

Other thicknesses, widths and separations may be used for the periodic acoustic grating 105, the uniform plate 110 and the resonant cavity 115 within the scope of this disclosure. Altering the various thicknesses, widths and/or separations may modify the transmission efficiency and/or the working wavelength associated of the acoustic diode 100. In particular, the working wavelength of the acoustic diode 100 may be associated with the thickness of the uniform plate 110 and/or the period of the gratings of the periodic acoustic grating 105. As such, the one-way effect may be realised within a particular frequency by appropriately choosing the geometrical parameters.

In an embodiment, the acoustic diode 100 may exhibit a coincidence effect for acoustic waves incident on the periodic acoustic grating 105. Under the coincidence effect for a uniform plate 110, acoustic waves in a fluid and flexural waves in a solid uniform plate should have equivalent values for the component of a wave vector tangential to the fluid-solid interface. A significant increase in the power transmission of acoustic waves at the coincidence frequency is a result of the resonant excitation of flexural waves, such that the acoustic energy can be radiated to the other side through the large resonant vibration of the uniform plate 110. The coincidence effect occurs upon the fluid-solid interface as long as the incident acoustic waves are from a specific coincidence angle θ determined by the formula:

$$\theta = \arcsin\left(\frac{c_p}{c_f}\right),$$

where $c_p$ and $c_f$ are the phase velocity of the uniform plate 110 and the sound velocity of the fluid, respectively.

Figures 2, 3:
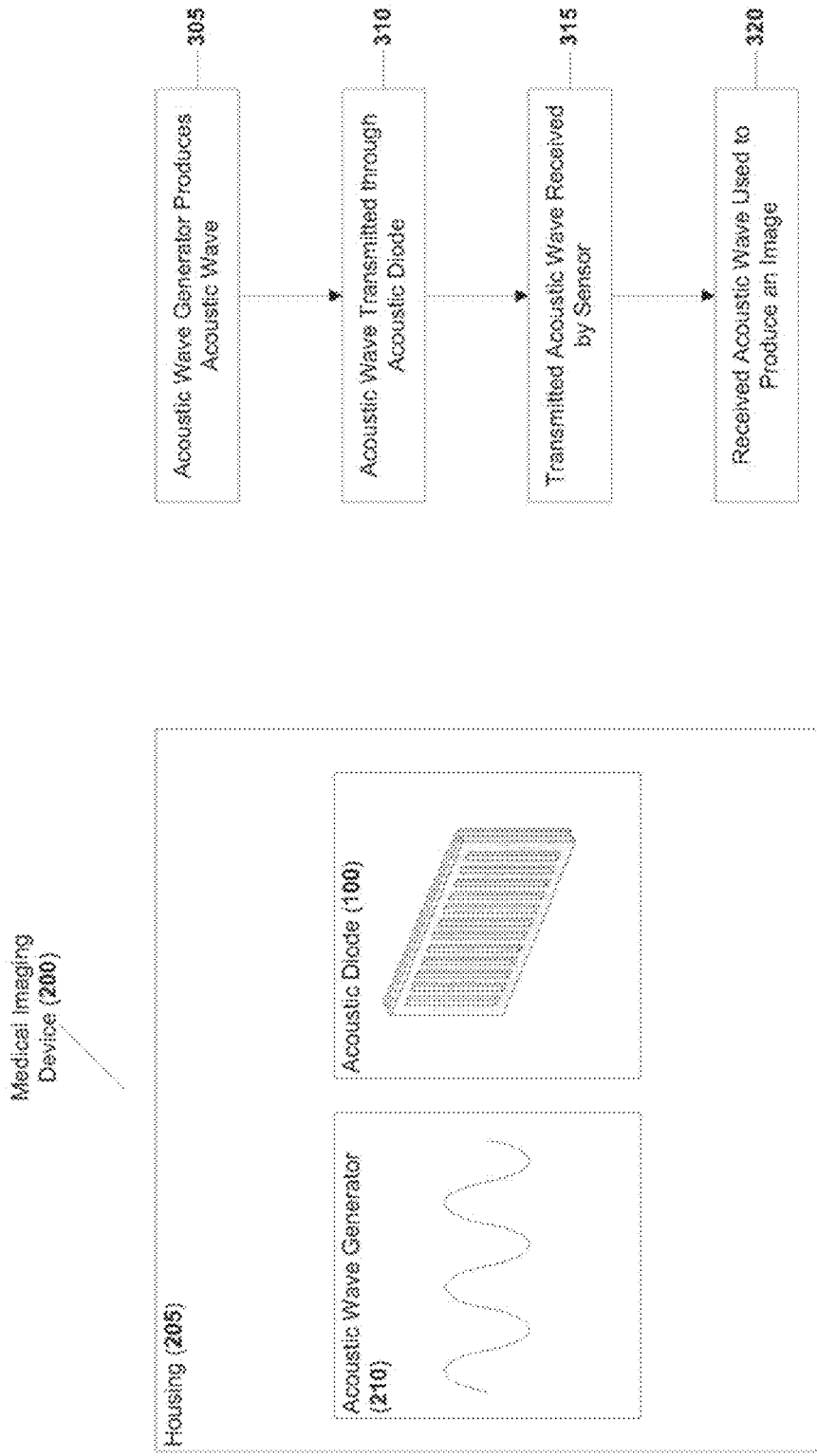
FIG. 2 depicts a block diagram of a medical imaging device incorporating an illustrative acoustic diode according to an embodiment.
FIG. 3 depicts a flow diagram of an illustrative method of using a medical imaging device according to an embodiment.

FIG. 2 depicts a block diagram of a medical imaging device incorporating an illustrative acoustic diode according to an embodiment. As shown in FIG. 2, the medical imaging device 200 may include a housing 205 surrounding an acoustic wave generator 210 configured to produce acoustic waves and an acoustic diode 100, such as is depicted in FIG. 1. The acoustic wave generator 210 may include one or more components configured to control the wavelengths produced by the medical imaging device 200. For example, the acoustic wave generator 210 may include a controller/processor, a tangible memory device, and/or the like. In an alternate embodiment, a controller/processor and/or a memory device may be located remotely from the acoustic wave generator 210 and transmit information via a wired or wireless connection. In an embodiment, the medical imaging device 200 may be an ultrasound imaging device. In an embodiment, the housing 205 of the medical imaging device 200 may be configured to be held by a user.

FIG. 3 depicts a flow diagram of an illustrative method of using a medical imaging device according to an embodiment. As shown in FIG. 3, an acoustic wave generator may produce 305 an acoustic wave having a wavelength. The wavelength of the acoustic wave may correspond to, for example and without limitation, an ultrasound frequency. For example, the acoustic wave may have a frequency of about 499 kHz to about 678 kHz. Other frequencies may also be used within the scope of this disclosure.

The acoustic wave may be transmitted 310 through an acoustic diode. In an embodiment, the acoustic diode may have a periodic acoustic grating and a uniform plate. The periodic acoustic grating may include a plurality of gratings. The uniform plate may be separated from the periodic acoustic grating by a resonant cavity. The acoustic diode may be configured to have a first transmission efficiency for acoustic waves incident on the periodic acoustic grating that is greater than a second transmission efficiency for acoustic waves incident on the uniform plate. When the acoustic wave is produced 305, it may be generated such that it becomes incident with the periodic acoustic grating of the acoustic diode and is transmitted 310 through the acoustic diode.

In an embodiment, the acoustic diode may further reflect substantially all acoustic waves incident with the uniform plate of the acoustic diode. In other words, acoustic waves that are not produced by the acoustic wave generator may not pass through the acoustic diode from the uniform plate side. As a result, the acoustic diode may limit interference from extraneous acoustic waves that are not produced as part of the medical imaging device.

The transmitted acoustic wave may be received 315 at a sensor. In an embodiment, the sensor may be configured to receive 315 acoustic waves generally. In an alternate embodiment, the sensor may be configured to receive 315 acoustic waves at the wavelength or wavelengths associated with the acoustic waves transmitted by the acoustic wave generator.

The received acoustic wave may be used 320 to produce an image. For example, if the acoustic wave generator is part of an ultrasound medical device, the received acoustic wave may be used 320 to produce an ultrasound image. Other images may be produced within the scope of this disclosure.

Figures 4, 5:
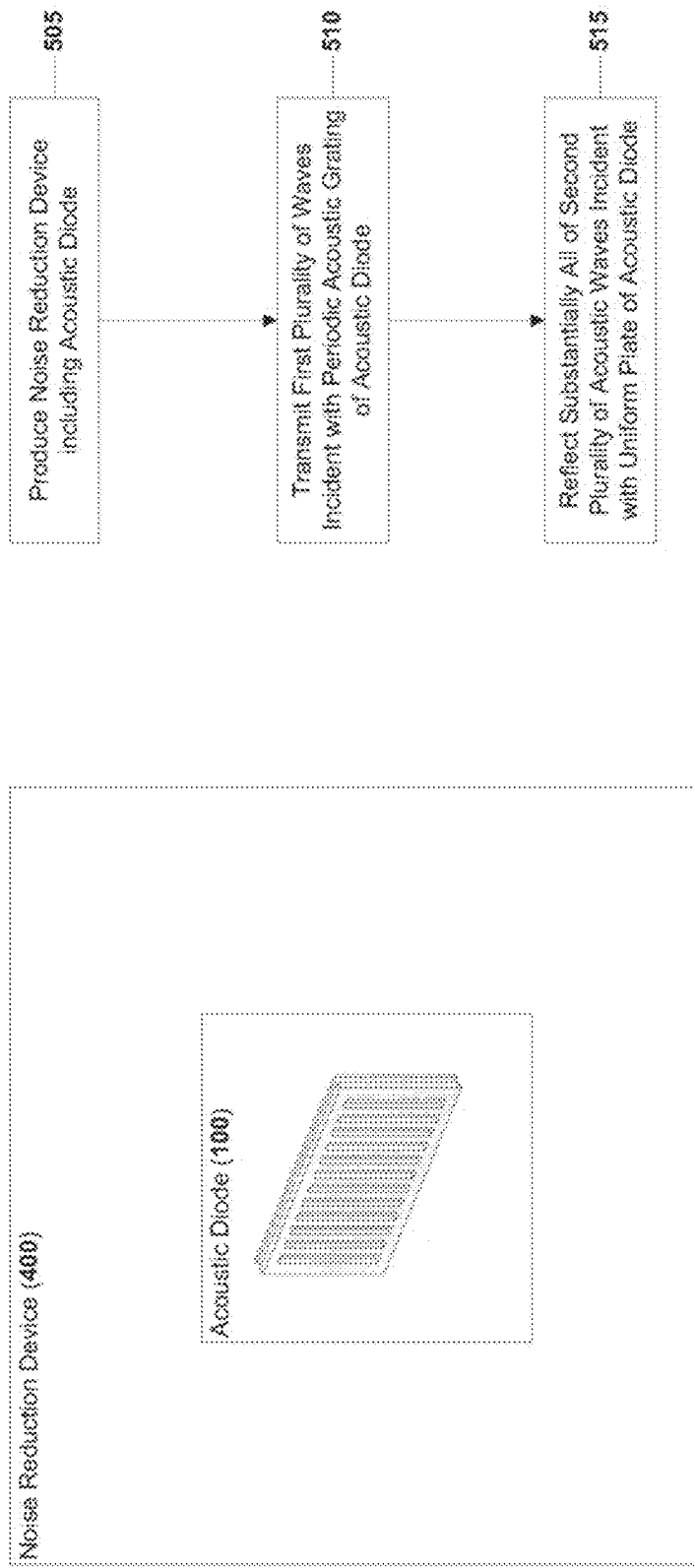
FIG. 4 depicts a block diagram of a noise reduction device incorporating an illustrative acoustic diode according to an embodiment.
FIG. 5 depicts a flow diagram of an illustrative method of reducing noise according to an embodiment.

FIG. 4 depicts a block diagram of a noise reduction device incorporating an illustrative acoustic diode according to an embodiment. As shown in FIG. 4, the noise reduction device 400 may include an acoustic diode 100, such as is depicted in FIG. 1. The acoustic diode 100 may be used to allow sound to pass in one direction through the noise reduction device 400, while restricting sound from passing through in the other direction. In this way, the acoustic diode may sound emanating from outside of the noise reduction device 400 to be substantially muted.

FIG. 5 depicts a flow diagram of an illustrative method of reducing noise according to an embodiment. As shown in FIG. 5, a noise reduction device including an acoustic diode may be produced 505. The acoustic diode may have a periodic acoustic grating and a uniform plate. The periodic acoustic grating may include a plurality of gratings. The uniform plate may be separated from the periodic acoustic grating by a resonant cavity. The acoustic diode is configured to have a first transmission efficiency for acoustic waves incident on the periodic acoustic grating and a second transmission efficiency for acoustic waves incident on the uniform plate. The first transmission efficiency may be greater than the second transmission efficiency for acoustic waves having a plurality of wavelengths. For example, acoustic waves for which the first transmission efficiency is greater than the second transmission efficiency may include acoustic waves having a frequency of about 499 kHz to about 678 kHz. Other frequencies may additionally or alternately have a greater first transmission efficiency within the scope of this disclosure.

At least a portion of a first plurality of acoustic waves incident with the periodic acoustic grating may be transmitted 510 through the noise reduction device. In an embodiment, the first transmission efficiency may be about 10% to about 60.8% for acoustic waves having a frequency of about 499 kHz to about 678 kHz. In an embodiment, the first transmission efficiency is greater than about 20%, on average, for acoustic waves having a frequency of about 499 kHz to about 678 kHz.

In contrast, substantially all of a second plurality of acoustic waves incident with the uniform plate of the noise reduction device may be reflected 515 by the noise reduction device. In an embodiment, the second transmission efficiency may be less than about 1%, on average, for acoustic waves having a frequency of about 499 kHz to about 678 kHz.

In this manner, a noise level may be reduced on a side of the acoustic diode faced by the periodic acoustic grating.

EXAMPLES

Example 1: Brass Acoustic Diode

An acoustic diode was constructed out of brass. The acoustic diode included a periodic acoustic grating having a plurality of gratings and a uniform plate. The width and thickness of each grating of the periodic acoustic grating were 1.5 mm and 3 mm, respectively. The distance between adjacent gratings of the periodic acoustic gratings was 6 mm. The thickness of the uniform plate was 1.5 mm. The uniform plate was separated from the periodic acoustic grating by 1.5 mm.

Example 2: Acoustic Diode Transmission and Reflectance of Acoustic Waves

Figures 6A, 6B, 6C:
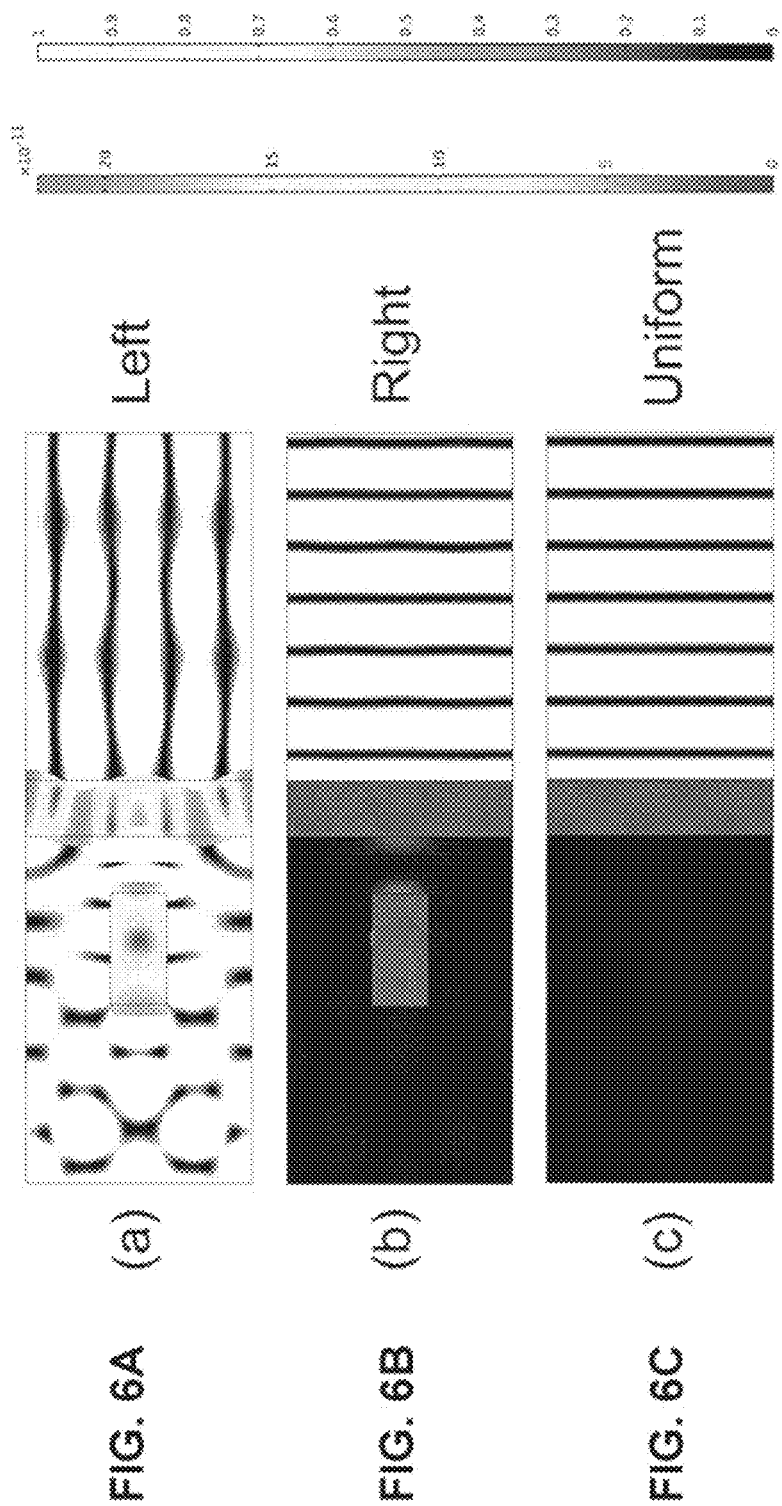
FIGS. 6A-C illustrate graphical depictions of the spatial intensity of an acoustic field and a total displacement field distribution for acoustic waves incident on a grating side of an acoustic diode, on a uniform plate side of the acoustic diode, and on a uniform plate, respectively, according to an embodiment.

The acoustic diode of Example 1 was immersed in water. The total length of the system including the water domain was 20 cm. The mass density of water and brass are 1000 kg/mm$^3$ and 8600 kg/m$^3$, respectively. The velocity of sound in water is 1498 m/s. The longitudinal and transversal velocities of sound in brass are 4000 m/s and 2100 m/s, respectively. FIG. 6A illustrates graphically the spatial intensity of an acoustic field and a total displacement field distribution for acoustic waves incident on a grating side of an acoustic diode. As shown in FIG. 6A, a substantial portion of the incident acoustic energy associated with acoustic waves incident on the grating side of the acoustic diode was transmitted through the acoustic diode. FIG. 6B illustrates graphically the spatial intensity of an acoustic field and a total displacement field distribution for acoustic waves incident on a uniform plate side of the acoustic diode. As shown in FIG. 6B, substantially all of the acoustic energy associated with acoustic waves incident on the uniform plate side of the acoustic diode was reflected by the acoustic diode. Indeed, the amount of acoustic energy incident with the uniform plate side of the acoustic grating that was transmitted and reflected by the acoustic diode was equivalent to an amount of acoustic energy incident with a reference uniform plate, as is shown in FIG. 6C. The amount of acoustic energy transmitted through a uniform brass plate was low because of the acoustic impedance mismatch between the brass and the water.

Figure 7A:
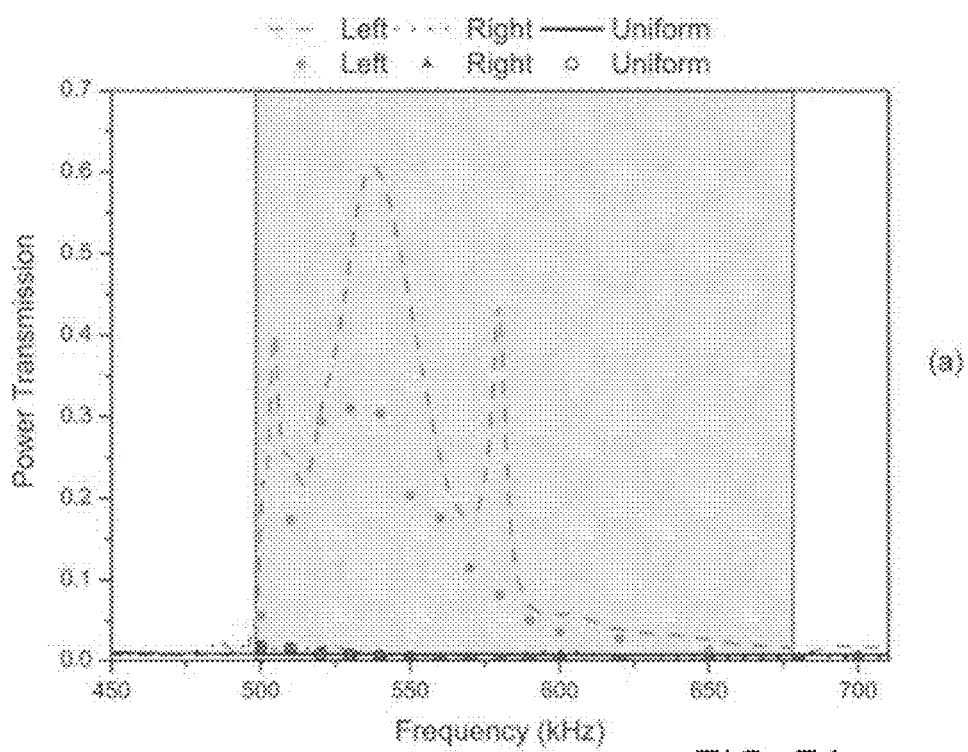
FIG. 7A depicts a graph of measured and simulated power transmission spectra for an acoustic diode according to an embodiment.

FIG. 7A depicts a graph of measured and simulated power transmission spectra for the acoustic diode of Example 1. As shown in FIG. 7A, acoustic energy of about 499 kHz to about 678 kHz incident with the periodic acoustic grating was transmitted through the acoustic diode at a substantially higher transmission efficiency than acoustic energy of about 499 kHz to about 678 kHz incident with the uniform plate of the acoustic diode or a reference uniform plate.

Figure 7B:
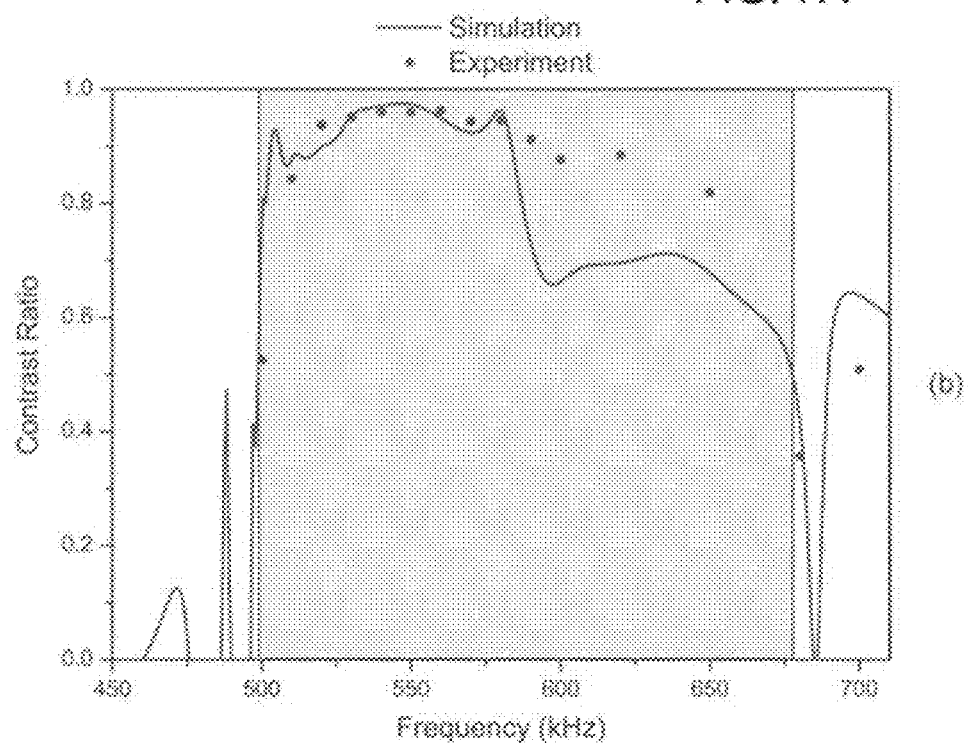
FIG. 7B depicts a graph of measured and simulated contrast ratios for an acoustic diode according to an embodiment.

FIG. 7B depicts a graph of measured and simulated contrast ratios for the acoustic diode of Example 1. The contrast ratio was determined by the formula $$R_c = \frac{T_L - T_R}{T_L + T_R},$$

where $T_L$ is the transmission efficiency for acoustic energy incident on the periodic acoustic grating of the acoustic diode of Example 1, and $T_R$ is the transmission efficiency for acoustic energy incident on the uniform plate of the acoustic diode of Example 1. The shaded areas of FIGS. 7A and 7B represent the frequencies at which the transmission ration is at least 0.5.

The difference between the transmission efficiency for acoustic energy incident on the periodic acoustic grating ($T_L$) and the transmission efficiency for acoustic energy incident on the uniform plate ($T_R$) represents the effectiveness of the acoustic diode in allowing acoustic waves to pass in a first direction and to impede acoustic waves from passing in an opposing direction. $T_L$ identities the ability for acoustic waves incident on the periodic acoustic grating to pass through the acoustic diode. $T_R$ identifies the ability for acoustic waves incident on the uniform plate to pass through the acoustic diode. Because $T_L$ is larger or substantially larger than $T_R$, a larger or substantially larger amount of acoustic energy incident on the periodic acoustic grating is passed through the acoustic diode than acoustic energy incident on the uniform plate.

Example 3: Ultrasound Device with Acoustic Diode

An ultrasound device will include an acoustic diode, such as the acoustic diode in Example 1, and an acoustic wave generator. The acoustic wave generator will operate under the control of a processor that directs the acoustic wave generator to generate acoustic waves at a particular time and/or at a particular frequency. The processor will be remotely located from the acoustic wave generator and in communication with the acoustic wave generator via a wired connection. The processor will further control an imaging device, such as a display screen, used to provide information to a user based on the defection of the acoustic waves at a sensor device.

In the above detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be used, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure. In addition to those enumerated herein, will be apparent to those skilled in the art from the foregoing descriptions. Such modifications and variations are intended to fail within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the contest and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups. It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc). In those instances where a convention analogous to "at least one of A, B, or C, etc," is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, or any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

The invention claimed is:

1. An acoustic diode comprising:
a periodic acoustic grating having a plurality of gratings; and
a uniform plate separated from the periodic acoustic grating by a resonant cavity,
wherein the acoustic diode is configured to have a first transmission efficiency for acoustic waves incident on the periodic acoustic grating that is greater than a second transmission efficiency for acoustic waves incident on the uniform plate, and
wherein the acoustic waves have a wavelength within a range of wavelengths.

2. The acoustic diode of claim 1, wherein at least one grating of the plurality of gratings has a width of about 1.5 millimeters.

3. The acoustic diode of claim 1, wherein a distance between adjacent gratings of the plurality of gratings is about 6 millimeters.

4. The acoustic diode of claim 1, wherein the periodic acoustic grating has a thickness of about 3 millimeters.

5. The acoustic diode of claim 1, wherein the uniform plate has a thickness of about 1.5 millimeters.

6. The acoustic diode of claim 1, wherein the resonant cavity has a thickness of about 1.5 millimeters.

7. The acoustic diode of claim 1, wherein the periodic acoustic grating comprises metal.

8. The acoustic diode of claim 1, wherein the uniform plate comprises metal.

9. The acoustic diode of claim 1, wherein the acoustic waves have a frequency of about 499 kHz to about 678 kHz.

10. The acoustic diode of claim 1, wherein the acoustic diode exhibits a coincidence effect for acoustic waves incident on the periodic acoustic grating, and wherein an outgoing angle of the acoustic wave is equal to $\arcsin(c_f/c_p)$, where $c_f$ is the velocity of the acoustic wave in the resonant cavity and $c_p$ is the velocity of the acoustic wave in the uniform plate.

11. The acoustic diode of claim 1, wherein the first transmission efficiency is about 10% to about 60.8% for acoustic waves having a frequency of about 499 kHz to about 678 kHz.

12. The acoustic diode of claim 1, wherein the first transmission efficiency is greater than about 20%, on average, for acoustic waves having a frequency of about 499 kHz to about 678 kHz.

13. The acoustic diode of claim 1, wherein the second transmission efficiency is less than 1%, on average, for acoustic waves having a frequency of about 499 kHz to about 678 kHz.

14. A medical imaging device comprising:
an acoustic wave generator configured to produce acoustic waves; and
an acoustic diode comprising:
a periodic acoustic grating having a plurality of gratings, and
a uniform plate separated from the periodic acoustic grating by a resonant cavity,
wherein the acoustic diode is configured to have a first transmission efficiency for acoustic waves incident on the periodic acoustic grating that is greater than a second transmission efficiency for acoustic waves incident on the uniform plate, and
wherein the acoustic waves have a wavelength within a range of wavelengths.

15. The medical imaging device of claim 14, wherein the acoustic diode exhibits a coincidence effect for acoustic waves incident on the periodic acoustic grating, and wherein an outgoing angle of the acoustic wave is equal to arcsin $(c_f/c_p)$, where $c_f$ is the velocity of the acoustic wave in the resonant cavity and $c_p$ is the velocity of the acoustic wave in the uniform plate.

16. The medical imaging device of claim 14, wherein the first transmission efficiency is about 10% to about 60.8% for acoustic waves having a frequency of about 499 kHz to about 678 kHz.

17. The medical imaging device of claim 14, wherein the first transmission efficiency is greater than about 20%, on average, for acoustic waves having a frequency of about 499 kHz to about 678 kHz.

18. The medical imaging device of claim 14, wherein the second transmission efficiency is less than 1%, on average, for acoustic waves having a frequency of about 499 kHz to about 678 kHz.

19. A method of performing medical imaging, the method comprising:
producing, by an acoustic wave generator in an ultrasound device, an acoustic wave having a wavelength within a range of wavelengths;
transmitting the acoustic wave through an acoustic diode, wherein the acoustic wave passes through a periodic acoustic grating of the acoustic diode and a uniform plate of the acoustic diode, wherein the periodic acoustic grating comprises a plurality of gratings, wherein the uniform plate is separated from the periodic acoustic grating by a resonant cavity, and wherein the acoustic diode is configured to have a first transmission efficiency for acoustic waves incident on the periodic acoustic grating that is greater than a second transmission efficiency for acoustic waves incident on the uniform plate;
receiving the transmitted acoustic wave at a sensor; and
using the received acoustic wave to produce an image.

20. The method of claim 19, further comprising:
reflecting substantially all acoustic waves incident on the uniform plate of the acoustic diode.

21. The method of claim 19, further comprising exhibiting, by the acoustic diode, a coincidence effect for acoustic waves incident on the periodic acoustic grating, wherein an outgoing angle of the acoustic wave is equal to arcsin $(c_f/c_p)$, where $c_f$ is the velocity of the acoustic wave in the resonant cavity and $c_p$ is the velocity of the acoustic wave in the uniform plate.

22. The method of claim 19, wherein transmitting the acoustic wave further comprises transmitting the acoustic wave such that the first transmission efficiency is about 10% to about 60.8% for acoustic waves having a frequency of about 499 kHz to about 678 kHz.

23. The method of claim 19, wherein transmitting the acoustic wave further comprises transmitting the acoustic wave such that the first transmission efficiency is greater than about 20%, on average, for acoustic waves having a frequency of about 499 kHz to about 678 kHz.

24. The method of claim 19, wherein transmitting the acoustic wave further comprises transmitting the acoustic wave such that the second transmission efficiency is less than 1%, on average, for acoustic waves having a frequency of about 499 kHz to about 678 kHz.

25. A method of reducing noise, the method comprising:
producing an acoustic diode having a periodic acoustic grating and a uniform plate, wherein the periodic acoustic grating comprises a plurality of gratings, and wherein the uniform plate is separated from the periodic acoustic grating by a resonant cavity;
transmitting at least a portion of a first plurality of acoustic waves incident on the periodic acoustic grating; and
reflecting substantially all of a second plurality of acoustic waves incident on the uniform plate of the acoustic diode,
wherein a noise level is reduced on a side of the acoustic diode faced by the periodic acoustic grating.

26. The method of claim 25, further comprising exhibiting, by the acoustic diode, a coincidence effect for acoustic waves incident on the periodic acoustic grating, wherein an outgoing angle of the acoustic wave is equal to arcsin $(c_f/c_p)$, where $c_f$ is the velocity of the acoustic wave in the resonant cavity and $c_p$ is the velocity of the acoustic wave in the uniform plate.

27. The method of claim 25, wherein transmitting at least a portion of the first plurality of acoustic waves further comprises transmitting such that a first transmission efficiency of the acoustic diode is about 10% to about 60.8% for acoustic waves having a frequency of about 499 kHz to about 678 kHz.

28. The method of claim 25, wherein transmitting at least a portion of the first plurality of acoustic waves further comprises transmitting such that a first transmission efficiency of the acoustic diode is greater than about 20%, on average, for acoustic waves having a frequency of about 499 kHz to about 678 kHz.

29. The method of claim 25, wherein transmitting at least a portion of the first plurality of acoustic waves further comprises transmitting such that a second transmission efficiency of the acoustic diode is less than 1%, on average, for acoustic waves having a frequency of about 499 kHz to about 678 kHz.

* * * * *